United States Patent [19]

Chun

[11] Patent Number: 5,142,969
[45] Date of Patent: Sep. 1, 1992

[54] KIMCHI FERMENTOR AND CONTROL SYSTEM THEREOF USING A KIMCHI CURING SENSOR

[75] Inventor: Jae K. Chun, Suweon, Rep. of Korea

[73] Assignee: Samsung Electronics Co., Ltd., Suweon, Rep. of Korea

[21] Appl. No.: 278,230

[22] Filed: Nov. 30, 1988

[30] Foreign Application Priority Data

May 27, 1988 [KR] Rep. of Korea .................. 6278

[51] Int. Cl.$^5$ .......................... C12H 1/00; A23B 4/00
[52] U.S. Cl. ..................................... 99/468; 99/470; 99/483; 99/486; 435/289; 435/291; 435/316
[58] Field of Search ................ 99/331, 276, 451, 468, 99/467, 470, 472, 483, 506, 486, 534, 493; 435/289, 290, 291, 316, 313; 426/615, 52, 49

[56] References Cited

U.S. PATENT DOCUMENTS

| | | |
|---|---|---|
| 3,753,731 | 8/1973 | Christ ................................... 99/472 |
| 3,809,618 | 5/1974 | Muller .................................. 435/316 |
| 3,978,918 | 9/1976 | Nagatomo et al. .................. 435/316 |
| 4,062,276 | 12/1977 | Stahmann ............................ 99/467 |
| 4,204,037 | 5/1980 | Dill et al. ............................ 435/290 |
| 4,293,655 | 10/1981 | Christ et al. .......................... 99/472 |
| 4,315,990 | 2/1982 | Sheets ................................. 435/289 |
| 4,318,992 | 3/1982 | Mila-de-la-Roca et al. ......... 435/291 |
| 4,692,414 | 9/1987 | Yamada et al. ...................... 435/291 |
| 4,746,615 | 5/1988 | Buchholtz et al. .................. 435/289 |
| 4,785,728 | 11/1988 | Miyata et al. ........................ 99/535 |

FOREIGN PATENT DOCUMENTS

| | | |
|---|---|---|
| 0056780 | 11/1988 | Japan ..................................... 99/535 |
| 0056781 | 11/1988 | Japan ..................................... 99/535 |
| 2032759 | 5/1980 | United Kingdom ................... 99/535 |

Primary Examiner—Timothy F. Simone
Attorney, Agent, or Firm—Robert E. Bushnell

[57] ABSTRACT

A kimchi fermentor and control system thereof using a kimchi curing sensor relates to a mass production of kimchi or naturally fermenting foods, in which the kimchi fermentor is provided with the kimchi barrel having the heater and the cooler mounted therein, the agitator and the electric circuit based on the microprocessor, otherwise the kimchi fermentor is adapted to a home refrigerator using the compressor and the fan in lieu of the cooler and agitator. Also in order to control the kimchi fermentor the microprocessor receives the signal having the control variables from the kimchi curing sensor and displays its operation mode according to the kimchi preparation method, the kimchi curing sensor is constructed to detect air bubbles and count the number of air bubbles so that the fermentation of kimchi is measured.

17 Claims, 8 Drawing Sheets

NO OF BUBBLES /1hr.

FIG. 10

NO OF BUBBLES /2hr.

KIMCHI FERMENTOR AND CONTROL SYSTEM THEREOF USING A KIMCHI CURING SENSOR

BACKGROUND OF THE INVENTION

The present invention relates to a kimchi fermentor, and particularly to a kimchi fermentor and control system thereof using kimchi curing sensor.

Kimchi is made of pickled vegetables including radish, cabbage and cucumber, and it is an indispensible dish in Korean cuisine. However, there have been numerous problems in its mass production and mass storage until now, because kimchi is a naturally fermented food and fermented kimchi has the defect of acidifying itself at room temperature.

Due to these problems, it is difficult to properly cure and produce kimchi on a commercial scale. While it is a fact that the problem of preserving properly cured kimchi for a long time has been encountered, it can not be said that kimchi is truly preserved as having its unique taste without controlling the fermentation for its curing. For example, with respect to the spread of refrigerator services for preserving kimchi, the frigerators have been used predominantly for preserving kimchi for long periods.

But kimchi stored in refrigerators is fermented even at relative low temperature. Also kimchi produces a unique odor which greatly influences other foodstuffs stored with it. Therefore, kimchi has not been produced to have the right taste in the refrigerator.

In light of this, it is an innovation if kimchi can be easily prepared to have the right taste, and the right taste can be preserved for a long time. Therefore, it is very ideal that kimchi has its degree of curing determined by means of a sensor, which can detect and measure the degree of curing of kimchi based on physiology and kimchi can be stored with the right taste for a long period.

But, the conventional method for automatically preparing kimchi includes only the steps of pickling kimchi and then controlling the fermentation period and temperature. Thus, the undesirable results have been caused as a result of either the kimchi manufacturing process or by the fermentation period and temperature, or the type of spice and the sauce quantity, etc.

That is to say, kimchi is a product with the sour taste of the organic acid obtained when the microorganism is increased in the pickled vegetable and the fermentation phenomenon occurs during the kimchi curing. It is well known that the taste of kimchi is greatly influenced by the type of the ,vegetable to be used, the type of the organism associated with kimchi, and the salt concentration and the temperature acting decisively to the increase of the number of microorganisms.

Thus, the design and construction of a kimchi fermentor must consider the fermentation physiology of kimchi. Also it has been the important task that in order to automatically manage the curing of kimchi, optimum control variables be derived to correspond to the degree of curing of kimchi. Then, the kimchi fermentation characteristics reported in Korea and overseas are its acidity or the pH. Thus the present invention aims at the design and construction of a kimchi fermentor, which uses the change in acidity pH as the measuring variables. But, if the acidity measuring equipment is installed in a home refrigerator, costs would be very expensive and uneconomical. Further, even if an acidity sensor is used in the refrigerator, the standard buffer solution must be used and thereby it can not remove the possibility that kimchi may be contaminated by the buffer solution. Also if the acidity electrode happens to be broken accidently, it can not prevent the risk that mercury and silver may cause serious contamination, because mercury and silver are the constituent parts of the electrodes. Therefore, it is very important that new variable capable of indicating kimchi curing should be founded.

Further, neverthless the variable adapted to the automatic control of kimchi fermentator has a problem in the measurement it must have a facility, which is easily converted into an electric signal having reliablity. Thus, it is further desirable for a kimchi fermentor to have a variable, which is economical and stable electric signal.

Thus, in order to find a variable adapted to kimchi curing, pressure changes relative to kimchi juice and the amount of gas produced during fermentation have been measured. That is, the representative physical change after preparing kimchi is to produce kimchi juice. Therefore it is known that changes in the amount of kimchi juice are easily measured and also are easily converted into electric signals, but it has been proven that the change of the amount of juice is caused by the protoplasm separation phenomenon and is in equilibrium sooner, whereas the amount of kimchi juice formed under various artificial temperatures and conditions have not for the most part been changed and influenced by the high or the low temperature. Thus it, has been known that the change in the amount of juice can not be used as a variable representing the beginning of kimchi curing or of the fermenting status.

Also, in connection with the amount of the gas generated while fermenting kimchi, it has been published that kimchi curing is closely related to the activities of microorganisms but is independent of acidity. Substantial kimchi fermentation mechanism makes the group of the un-aerobic or facultative microorganism, including *Lactobacillus plantarum*, which dissimilates the vegetables directly by or the microorganism increase in the basic dissoluable filtered solution to produce the organic acid and $CO_2$. At that time the concentration of the organic acid is representing the acidity, which had been broadly used as the index of kimchi curing. Thus it is found that if a method for effectively measuring the amount of such $CO_2$ produced is developed, it has the high possibility of the practical application as a index of kimchi curing as much as acidity value is usually used. Especially the gas measurement is more easily performed than the acidity measurement but also the cost for constructing a gas measuring appartus can be realized at low prices.

Accordingly, a pressure cell was used to measure the amount of the gas produced by fermenting kimchi, in which a kimchi sample is put in the pressure cell and then this pressure cell is again inserted into the case having kimchi to be fermented. Herein it is noted that the pressure cell has a capillary tube connected to the transducer which measures the pressure and converts the pressure into an electric signal. Therefore the pressure produced in the pressure cell was measured through the capillary tube at the transducer. As a result, it was experimentally confirmed that the pressure in the cell had been representing a curve similar to that of the microorganism increase, but after the lapse of 24's times the pressure in the cell had not been further changed During this experiment, kimchi had its acidic taste when the pressure in the cell was at the highest level. Its taste was equal to that of kimchi when the $CO_2$ gas is produced at the largest quantity.

Therefore it has been proven that the pressure cell can be used as the sensor for sensing the kimchi curing, but, it must prove the reproducibilty of the measure in order to be useful as a sensor. As to it, it had been observed whether the amount of kimchi sampled from the prepared kimchi is fermented in the sensor cell and which prepared kimchi is put in a kimchi case along with the sensor cell. As a result, it has been found that since the fermentation of kimchi is not relative to true cultivation but to natural increasement, the growth aspects of the bacterium differ between kimchi in a case and kimchi samples in the kimchi sensor was developed in accordance with the lapse of the fermenting time even though the same samples were used at the time being intended to prepare kimchi. That is, because the growth environment of the bacterium in the pressure cell is different from the growth environment of the bacterium in the kimchi case, the possibility for inhibiting the growth of the bacterium by the influence of the pressure in the cell cannot be overlooked. Thus the pressure cell does not have the same reproducibility as the sensor for sensing kimchi curing.

In the procedures of these studies, it has been found that kimchi induces generative of gas during fermentation, the gas generated as the products of the basic disassimilating metabolism and the respiration of the microorganism is dissolved in part in the kimchi solution but is mostly discharged out of the kimchi solution forming an air bubble. Then it has been observed that the generation of the air bubble is usually not performed at the beginning of the fermentation having the relatively lower concentration of the bacterium but upon reaching the logarithmic growth phase, air bubbles are significantly increased in the size and number and become capable of being seen with the naked eye. The present invention requires appartus which can collect the gas with the kimchi case being opened in order to overcome the disadvantages causing the failure of the control system due to the air explosure of the kimchi case due to less than perfect sealing of the pressure cell.

Considering these points, it should be noted that the sensor for sensing kimchi curing may have variables according to the kimchi preparing, if the sensor has the reproducibility and senses the curing degree of kimchi under various temperatures and conditions. Thus if this kimchi curing sensor is developed, a kimchi fermentor is easily constructed. Also a kimchi fermentor must be easily controlled by its system on the basis of the varibles obtained from the kimchi curing sensor. Since the kimchi fermentor designed or configured on the basis of the fermenting process, the fermenting procedure must be accurately measured, and kimchi fermenting status and environment must be controlled before executing the design of the refrigerator. Also the design of the kimchi fermentor must not ignore the growth characteristics of the microorganism and includes physiological characteristics, the mechanical characteristics and the electronic characteristics that is the control system, considered as one system. For example, it takes about one week to complete the procedures including the steps of pickling kimchi and curing it through the fermentation. Further kimchi fermentation must be accompanied through reiterated experiments because it is not a true cultivation which has its properly configured method relative to the automatic fermenting system of kimchi. Therefore the fermenting control system kimchi must include all parts substantially required for the design of a kimchi fermentor as well as the measuring and controlling systems.

SUMMARY OF THE INVENTION

In light of this, the primary object of the present invention is to provide a new kimchi curing sensor for sensing the degree of kimchi curing in the control system and converting that information into an electric signal.

Another object of the present invention is to provide a kimchi fermentor including the heating device and the cooling device to control kimchi fermentation, and the agitator facilitating the temperature to be balanced in the kimchi case in view of the fact that kimchi curing is largely influenced by the increase of the microorganism and the growth of the microorganism is influenced on the cultivation temperature.

Another object of the present invention is to provide a control system for independently controlling the heater, cooler and agitator so that the constant temperature is maintained at the error range of $+/-0.5°$ C. relative to various temperature range and such temperature range can be programmed.

Accordingly, the kimchi curing sensor of the present invention includes the following:

An easily constructed air bubble collecting apparatus made of plastic preventing the deterioration caused due to contacting kimchi for a long time.

An air bubble homogeneity apparatus made of material facilitating the air bubble to move from collecting apparatus and in form of the tube having the diameter of 5-8 mm.

A measuring apparatus for counting the number of the air bubbles including a photo interruptor and a binary counter for counting the frequency of the interruptions during the operation of the interruptor.

Also the kimchi fermentor of the present invention can use a conventional refrigerator by establishing the standardization of other conditions except for the temperature with respect to kimchi samples in view of the fact that kimchi fermentation is considered, as a natural fermentation, and the present invention includes the following:

at least one kimchi case having the curing sensor which is installed in the refrigerator to control kimchi curing, at least one fermenting barrel including the heating means, the agitating means and the cooling coils connected to each other for controlling the cooling therein, a kimchi curing fermenting control system controlling kimchi fermentation in accordance with a signal from the temperature sensor which is in the barrel and the kimchi curing sensor, and a cooling apparatus and a number of relays controlling the operation of the heating means and the cooling coil installed in the barrel in accordance with the control signal of the control system.

Also, a kimchi curing fermenting control system of the present invention includes the following;

a micom for detecting the degree of kimchi curing in accordance with kimchi fermenting and forcing the cured kimchi to store in the refrigerating states, an operating portion for operating the compressor and fan motor of the refrigerator, and the heating means according to the present invention, a controlling portion for controlling operating portion, a kimchi curing sensing portion for receiving the sensing signal from kimchi curing sensor and inputting the square wave to micom, an temperature sensing portion for converting into an digital signal an analog signal given from the temperature sensor installed in the fermenting barrel in accordance with the predetermined temperature, an displaying portion for showing the operation mode of the kimchi fermenting controlling system in accordance with the curing degree.

Thus the present invention is operated in accordance with the following kimchi preparing method;

performing the initialization work to adjust the fermentation level selected by the key input and selecting the corresponding function, judging what mode is operated among the strong mode, the middle mode and the weak mode of the fermentation control based on whether the temperature set through the fermentation selection is higher than the predetermined temperature and displaying the fermenting level relative with the fermenting states on the outside following turning on the heating means, counting the air bubbles and adjusting the temperature of the refrigerator at the predetermined fermentation temperature if the fermentation time is not lapped over the predetermined time.

judging whether the number of air bubbles divided by the predetermined times is larger than that of the air bubbles counted before the predetermined time, if the fermentation times is lapped over the predetermined times.

Storing the current count of air bubbles in the memory if the number of the air bubbles is larger than that of the predetermined number and adjusting the temperature of the refrigerator at the predetermined temperature.

Performing the weak mode of the fermentation when the peak points of air bubbles appears secondly as well as the standardization when the peak point of air bubbles appears thirdly, based on what times the peak states of air bubbles occur if the number of air bubbles is smaller than that of the air bubble, and cancelling the fermentation function under the standardization mode of the fermentation.

And at the last step kimchi is stored under the refrigerating condition.

BRIEF DESCRIPTION OF THE DRAWINGS

The above objects and other features of the invention will be seen with reference to the description taken in connection with the accompanying drawings, in which.

DETAILED DESCRIPTION

Figure 1:
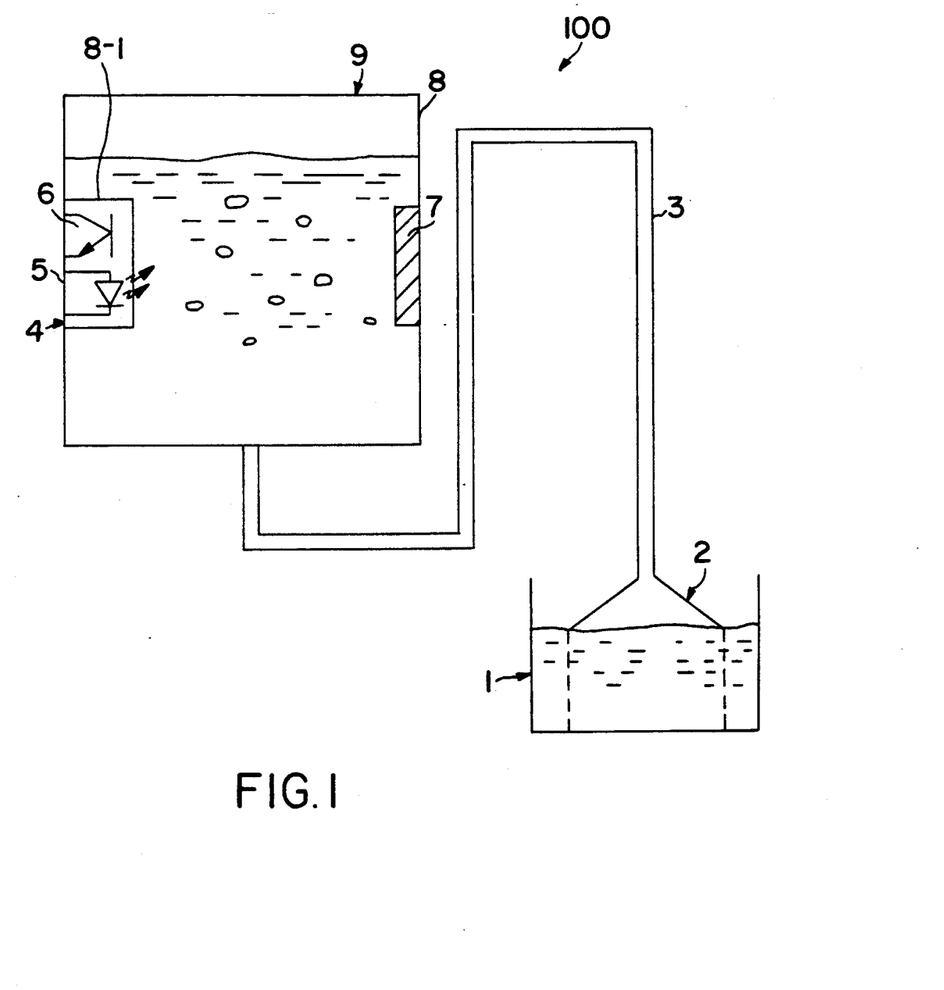
FIG. 1 is a schematic view theoretically representing the kimchi curing sensor according to the present invention.

FIG. 1 shows kimchi curing sensor 100 of the present invention. Kimchi curing sensor 100 includes a binary counter (not shown), air collecting portion 2, air bubble homogenium portion 3 case structure 8 and air bubble measuring portion 9. The air bubble collecting portion is made of plastic in the form of the funnel over kimchi case 1. Air bubble homogenium portion 2 is made of Teflon to transfer the air bubble therein and render the size of the air bubble. Case structure 8 is in form of a box having its lower portion coupled to air bubble collecting a portion 2 which is the transferring tube of the air bubble and receives the transparent liquid solution up to a predetermined height therein. Transparent case 8-1 is sealingly mounted to one wall of case structure 8, which is provided with a photo interruptor 4 including a photo diode 5 and photo transistor 6 therein. Reflecting film 7 such as a silver paper is attached to other wall opposite to the wall. Even though it is not shown in the drawing, the binary counter is connected to photo interruptor 4 and bubble measuring portion 9 is connected to the micom (not shown.

Figure 2A:
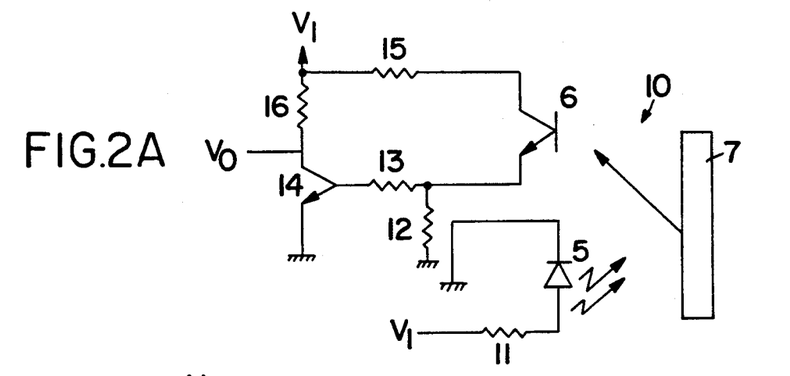
FIGS. 2A, 2B, 3A and 3B are schematic operating views representing the operation principle of the kimchi curing sensor according to the present invention.
Figure 2B:
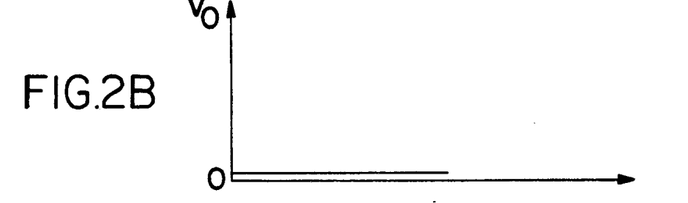

Air bubble measuring portion 9 and its operational characteristics are shown in FIGS. 2A, 2B and FIGS. 3A, 3B. Photo interruptor 4 is operated when power source V1 is applied through resistor 11 to photo diode 5. Photo diode 5 is lit and if the light is reflected by reflecting film 7, photo transistor 6 receives the reflecting light. At this time photo transistor 6 is triggered so that power source V1 is applied through resistor 15 to the base of transistor 14 by way of resistors 13 and 12. Transistor 14 is triggered to output power source voltage V0 through resistor 16. This voltage represents the non-detecting status of the circuit as no air bubble is shown in FIG. 2a. In other words, due to the operation of transistor 14 power source voltage V0 is grounded.

Figure 3A:
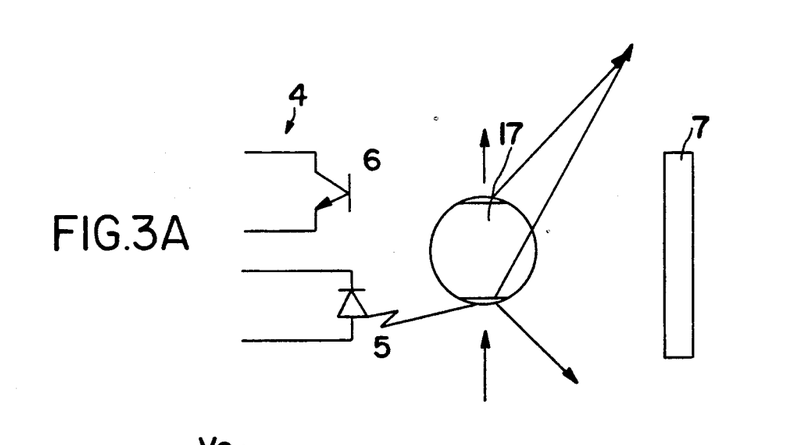
Figure 3B:
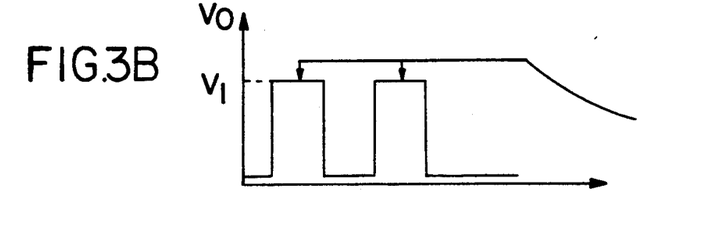

Then as shown in FIG. 3A the light of photo diode 5 is diffused by air bubble 17 when the air bubble is produced and screens the light so that the diffused light does not reach photo transistor 6. Photo interruptor 4 is not operated since the light diffused by air bubble 17 is not applied to photo transistor 6 as shown in FIGS. 3A and 3B. Accordingly measuring portion 10 produces the pulse signal and power source V1 is dropped by means of resistor 16 to output voltage but is reduced to ground potential when photo transistor 6 is not screened by air bubble 17 as shown in FIG. 3B.

Therefore, it is well known that kimchi curing sensor 100 helps to easily measure the amount of the air bubbles produced during fermenting kimchi and produce the following results.

Figure 9:
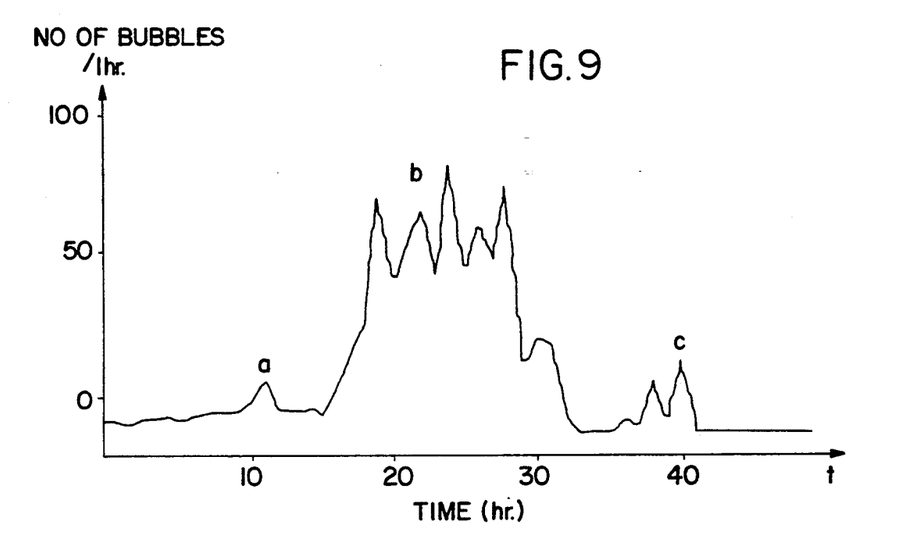
FIG. 9 is a graph representing the number of the air bubbles formed by the kimchi curing sensor per one hour.
Figure 10:
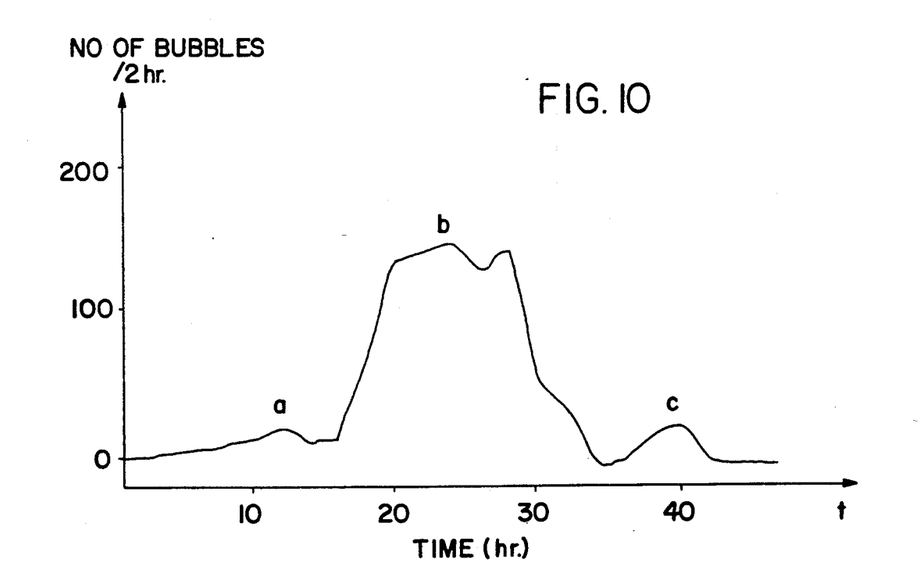
FIG. 10 is a graph representing the number of the air bubbles formed by the kimchi curing sensor per two hours.

That is to say, the specific kimchi curing curve as shown in FIG. 9 and FIG. 10 may be obtained with a result that the rate of, air bubble production is drawn as the number of the air bubbles produced according to the lapse of the fermenting time when kimchi curing sensor 100 is mounted on the kimchi case having kimchi fermented at 25° C. in order to test the capacity of measuring the amount of air bubbles by kimchi curing sensor 100 during fermentation.

FIG. 9 is a curve drawn on the basis of the number of air bubbles produced per hour, and FIG. 10 is a curve drawn on the basis of the number of the air bubble produced every two hours.

As shown in the drawings, it is noted that some peak points have appeared. In connection with FIG. 10, it is known that the curve of air bubbles production rate drawn at every two hours represents kimchi fermentation characteristics superior to those in FIG. 9. For example, the relative power peak a at the beginning of the fermentation represents he starting of the fermentation, and after twenty four hours the main peak b appears. At this time, the main fermentation is prosperously occurring. But when the period for counting air bubbles production rate is relatively shorter, the speed rate represents a very irregular aspect, and on the contrary, when the period is relatively longer, the rate curve shows a regular aspect. Herein the first peak point a is the starting point of the kimchi curing, the second peak point b represents the prosperous curing of kimchi, and the third peak point c is the last step which indicates that kimchi fermentation is completed.

Figure 11:
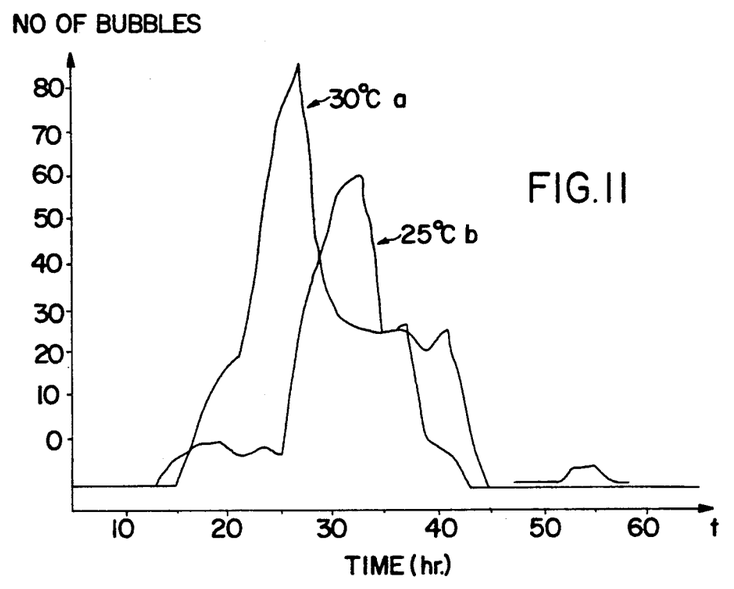
FIG. 11 is a graph representing the effect of the temperature at both of 30° C. and 25° C. with respect to the kimchi fermentation curve.

On the other hand, with a result that under various kimchi fermentation temperature the procedure of kimchi curing was investigated on the basis of air production rate, the curve as shown in FIG. 11 is a rate at which air bubbles are proved, in which the fermentation temperature is 25° C. and then 30° C. These curve forms are similar to each other even in any test method but it is known that the higher the temperature becomes, the earlier it the peak point representative of the beginning of the fermentation appears and the period of the main fermentation. Such results reflects the normal tendency that the temperature accelerates fermentation.

Figure 12:
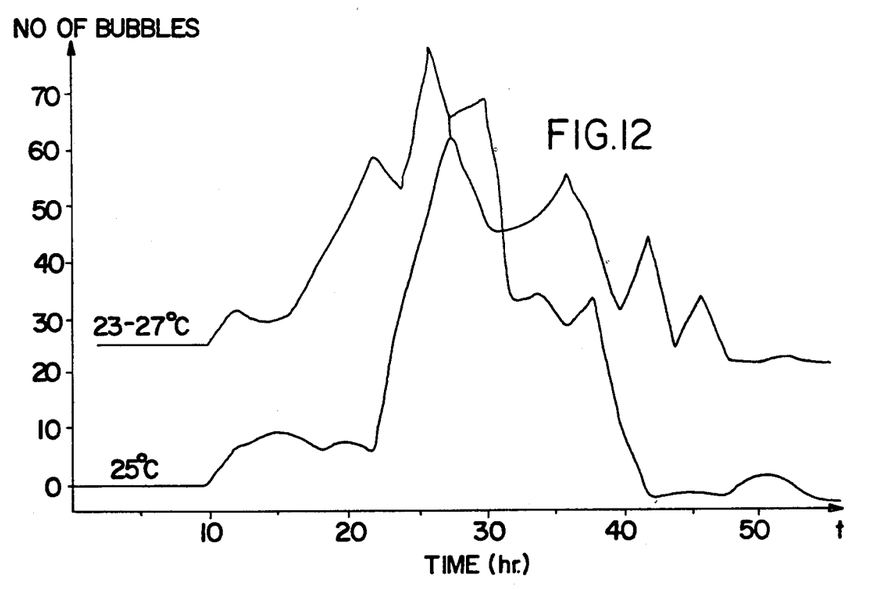
FIG. 12 is a graph representing the circumferential temperatures effect with respect to the count of air bubbles obtained by kimchi curing sensor during fermentation.

Also, as shown in FIG. 12, it may be a practical application that is able to test the capacity for measuring air bubbles under any environment condition variously changed by kimchi fermentor preceding to the use of the kimchi curing sensor in the kimchi fermentor or refrigerator and to sense kimchi curing, under these conditions. In order to accomplish these objects, a kimchi preparing control system is equipped with the program relative to the temperature change so that while kimchi is fermented in the barrel, the temperature of which is controlled between ±2° C. by turning said system on or off. When kimchi curing sensor 100 is mounted on the barrel, the signal measuring the air producing speed is identified in FIG. 12. That is, the curve showing the initially lower line in the drawing represents the result at a constant temperature of 25° C. and the solid curve in the drawing represents the result under the temperature changes between 25±220 C. It certifies that the kimchi curing sensor of the present invention is adequate when used under the temperature environment of the refrigerator changing in the range of 2°-3° C. Accordingly, the present invention can use a conventional refrigerator. Therefore it is needed for constructing refrigerators in which the new kimchi fermenting barrel is to be installed, because it is necessary to adjust the kimchi curing temperature in light of the fact that kimchi is a naturally fermenting food and it is very important to maintain the same environmental condition except for the temperature.

Figure 4:
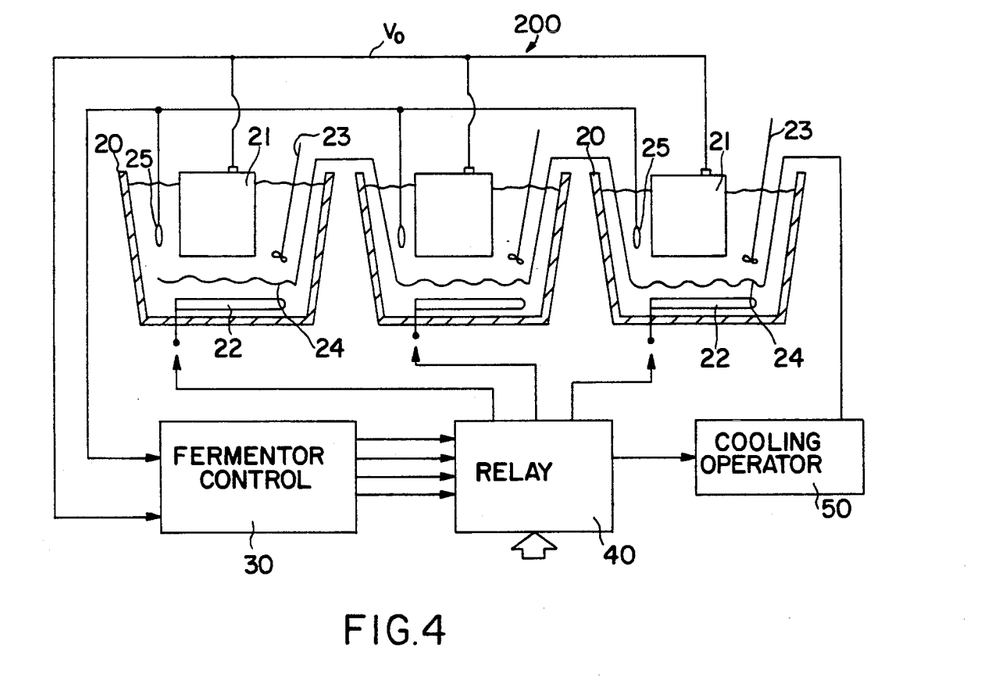
FIG. 4 is a view theoretically representing the kimchi fermentor according to the present invention.

For this reason, the fermentor of the present invention is provided with kimchi fermenting barrel 20 which maintains the same fermenting conditions except for the temperature. As shown in FIG. 4, kimchi fermenting barrel 20 is provided with a kimchi case, in which kimchi is put and kimchi curing sensor 100 (not shown) is installed. Heater 22 controls kimchi fermentation. Also, agitator 23 is mounted near the inner peripheral wall of kimchi case 21 to uniformly transfer the temperature around the wall. Cooling coil 24 is mounted in kimchi fermenting barrel 20 to cool the kimchi in kimchi case 21 in order to be changed into a storage mode when kimchi is completely cured. Temperature sensor 25 is installed in the kimchi fermenting barrel to detect the temperature therein. Therefore, kimchi curing fermenting control 30 receives the fermenting signal from kimchi curing sensor 100 and the temperature signal from temperature sensor 25 so that it controls relay operating portion 40 to operate heater 22 or cooling operating portion 50. Thereby it is known that kimchi fermentor 200 is provided with at least one kimchi fermenting barrel for the mass production of kimchi.

Figure 5:
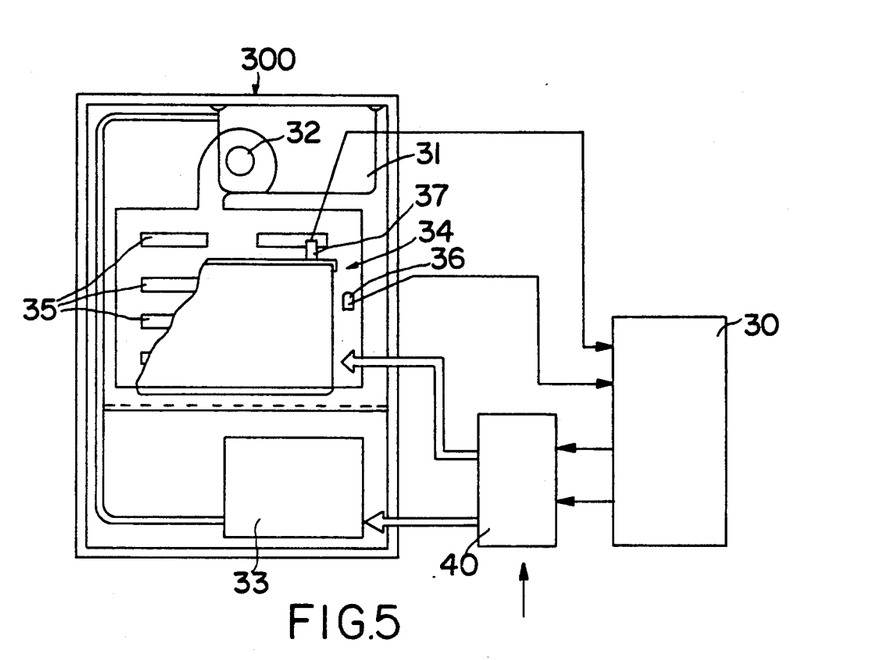
FIG. 5 and FIGS. 6A and 6B are a crossectional view, and a front view and side view representing the embodiment which kimchi fermentor of the present invention is adapted to the refrigerator.
Figure 6A:
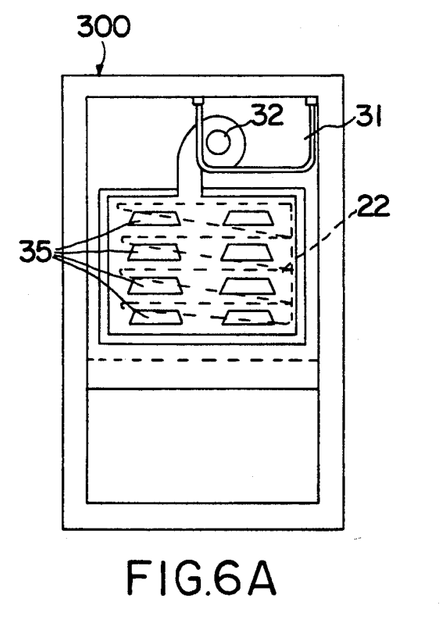
Figure 6B:
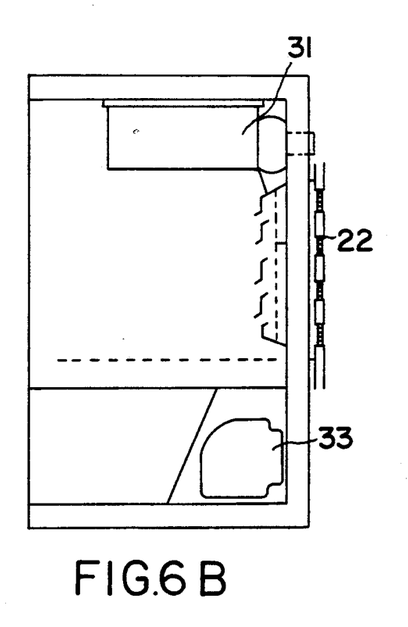

On the other hand, as shown in FIG. 5 and FIGS 6A and 6B, if the kimchi fermentor of the present invention is adapted to the home refrigerator, refrigerator 300 is provided with evaporator 31 installed on its upper portion of such a conventional configuration. Fan 32 is mounted adjacent to evaporator 31. Compressor 33 is installed in the lower portion of refrigerator and is connected to operate with evaporator 31.

A number of kimchi cases 35 are properly arranged in refrigerating chamber 34 along with temperature sensor 36 and kimchi curing sensor 37. Herein kimchi curing sensor 37 may be mounted in a number of kimchi cases 35, or at the outside of refrigerating chamber 31. Also heater 22 is mounted on the rear portion of kimchi case 35 in refrigerating chamber 31 as shown in FIG. 6 A,B, or into the inner portion of kimchi cases 35, respectively. Therefore, it is known that a home refrigerator may force fan 32 and evaporator 31 to perform the operation of the temperature equilibrium in lieu of agitator 23 and cooler 24 as shown in FIG. 4. The signal from temperature sensor 36 and kimchi curing sensor 37 is applied to kimchi fermenting control portion 30 similar to the device of FIG. 4. Relay operating portion 40 is operated according to the signal of kimchi fermenting control portion 30 configured so as to control compresser 33, fan 32 and evaporator 31.

Figure 7:
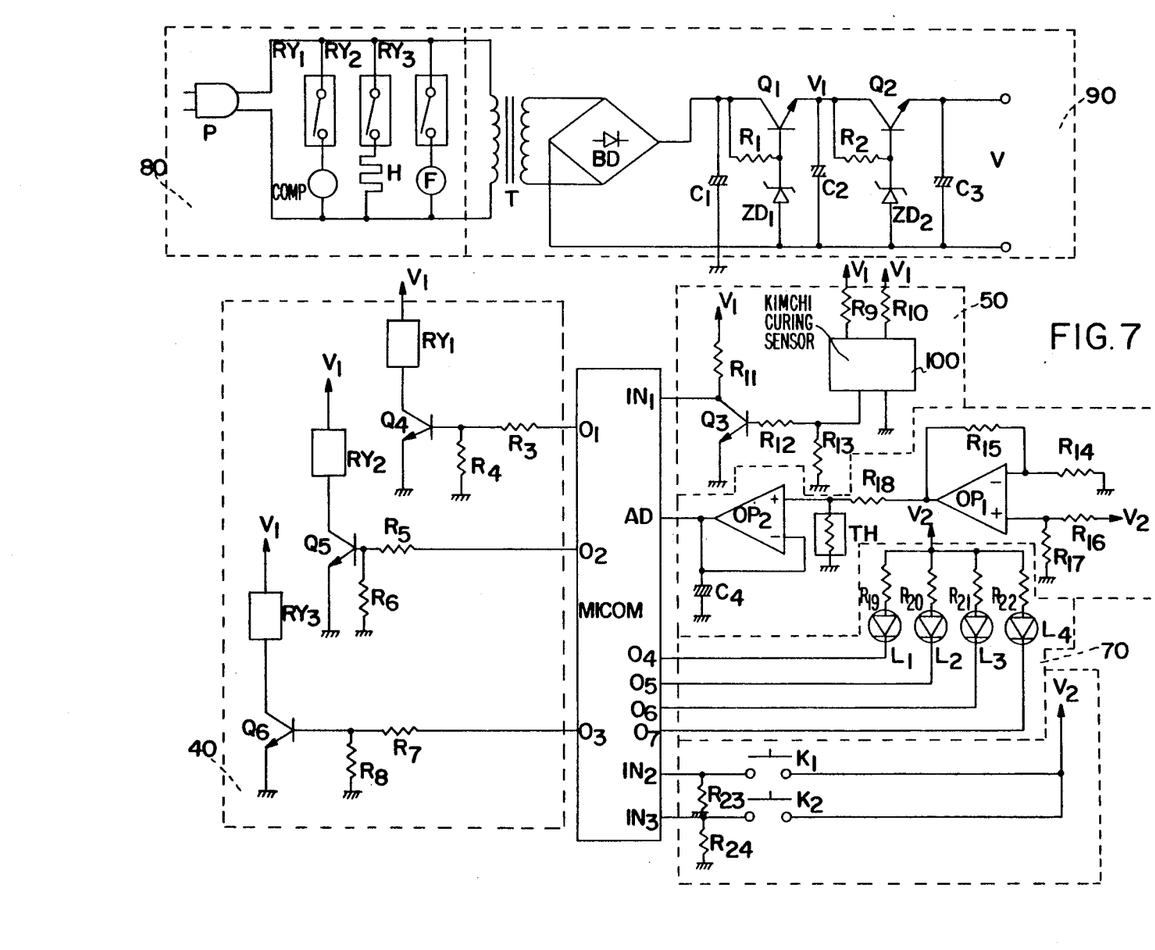
FIG. 7 is detailed circuit representing the kimchi preparation control system according to the present invention.

Accordingly, kimchi fermentors 200 and 300 of such like configurations are controlled by kimchi fermenting control system 30 as shown in FIG. 7.

In FIG. 7, kimchi fermenting control system 30 includes micom IC1. This micom IC1 has inputting terminals IN2 AND IN3 connected in full down form by means of resistors R23 and R24 to key switches K1 and K2 to be initialized in itself, respectively. Kimchi curing sensing portion 50 is connected to inputting terminal IN1 of micom IC1. Kimchi curing sensing portion 50 is provided with kimchi curing sensor 100 connected to resistors R9 and R10 that receive the power source voltage V1. The output from sensor 100 is applied through resistors R12 and R13 to the base of transistor Q3. Transistor Q3 has the emitter grounded, and the collector connected through resistor R11 to power source V1 is connected directly to input terminal IN1, so that the signal like the pulse wave of FIGS. 3A and 3B from kimchi curing sensor 100 according to the production of the air bubbles is applied to make micom IC1 count the pulses. Temperature sensing portion 60 is connection to A/D terminal AD. This temperature sensing portion 60 is provided with operating amplifier OP1 for producing the reference voltage. The non-inverting terminal of operating amplifier OP1 is connected through resistors R17 and R16 to power source V2 and the inverting terminal of operating amplifier OP1 is connected through resistor R14 to the ground and through resistor R15 in feedback form to the output terminal of operating amplifier OP1. The reference voltage of operating amplifier OP1 is applied through resistor R18 to the non-inverting terminal of operating amplifier OP2, in which resistor R18 is connected in parallel to temperature sensor TH of a thermistor, and the output voltage from operating amplifier OP1 is increased or dropped according to the sensing states of temperature sensor TH. Operating amplifier OP2 has the non-inverting terminal connected in the feedback form to its output terminal and through condenser C1 to the ground, so that the sensing signal from temperature sensor TH is input to analog/digital(A/D) terminal AD so as to measure the temperature in the fermenting barrel of a kimchi fermentor or the refrigerating chamber of the refrigerator.

Display portion 70 includes light emitting diodes L1-L4 connected to output terminal 04-07 of micom IC1, the other end of which is connected through resistors R19-R22 to power source V2. Thus, each of the light emitting diodes L1-L4 displays the operation states of strong mode, weak mode and standardization mode or the storing mode in kimchi fermenting.

Relay operating portion 40 includes relay RY1, RY2 and RY3, each of which can apply the power source to the compressor, the heater and the fan, respectively. These relays RY1, RY2 and RY3 respectively have one end connected to power source V1 and other end connected to each of the collectors of transistor Q4,Q5 and Q6. Transistors Q4, Q5 and Q6 have their bases connected through resistor R4,R5,R6,R7 and R6 to outputs O1, O2 and O3 of micom IC1, respectively. Thus, relays RY1, RY2 and RY3 are operated according to the controls of micom IC1. Also relays RY1, RY2 and RY3 are coupled so as to control the operation of compressor COMP, heater H and fan F connected in parallel to the primary winding portion of transformer T, respectively, and are configured as the relay operating portion 40 along with compressor COMP, heater H and fan F.

Power source portion 90 includes transformer T, the second winding portion of which is connected to bridge circuit BD. The output terminal of bridge circuit BD is connected to smoothing condenser C1, at the back portion of which the constant voltage circuit is formed. For example, the collector of transistor Q1 is connected to bridge circuit BD, resistor R1 is connected between the collector and emitter of transistor Q1, and the base of transistor Q1 is connected to zener diode ZD1, the cathode of which is grounded. Thus, transistor Q1 outputs the power source voltage V1.

At the back portion of power source V1 connected to smoothing condenser C2, the constant voltage circuit with respect to the power source V2 is constructed, in which the collector of transistor Q2 is connected to the emitter of transistor Q1, Resistor R2 is connected between the base and collector of transistor Q2, and zener diode ZD2 is connected to the base of transistor Q2. Thus transistor Q2 outputs the power source voltage V2 through smoothing condenser C3.

Figure 8:
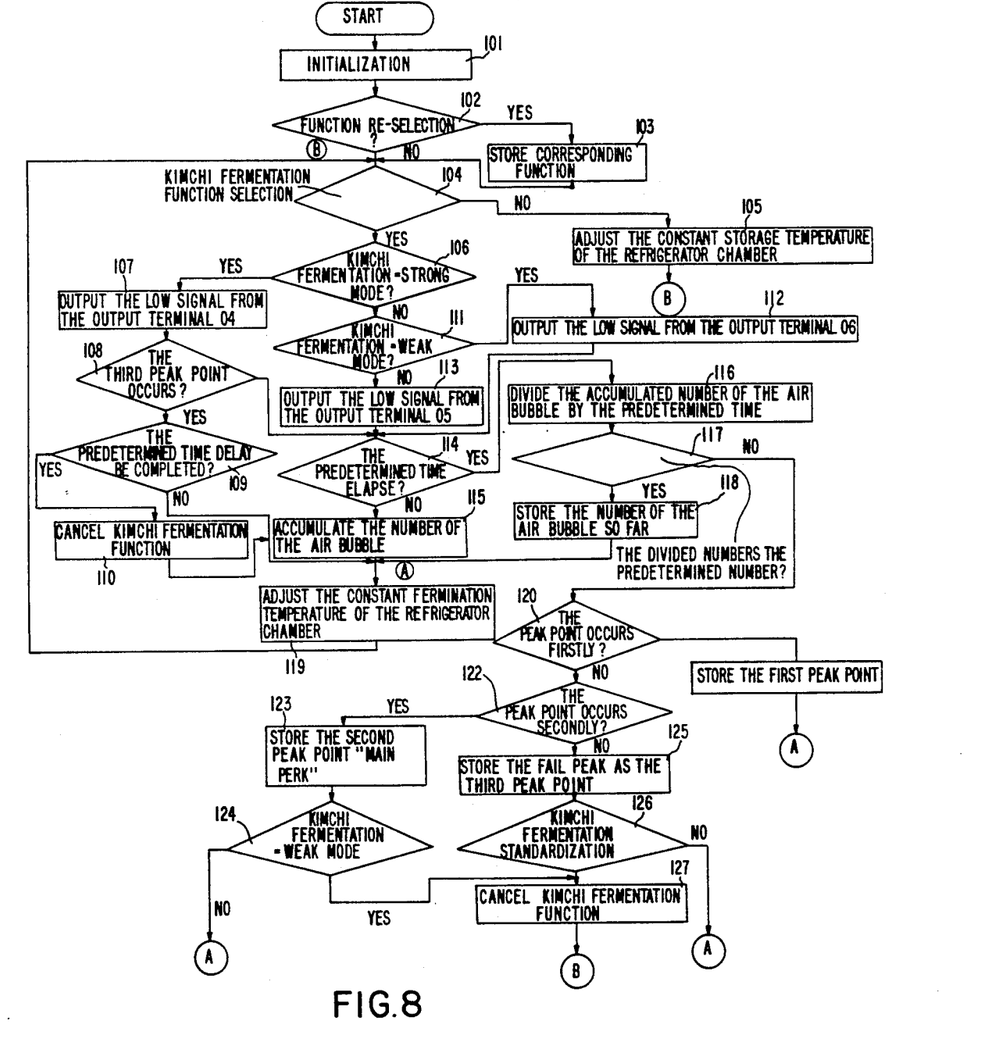
FIG. 8 is a flow chart representing the control method of the kimchi fermentor according to the present invention.

Referring now to FIG. 8, fermenting control system 30 of the present invention as described above firstly performs the initialization work of micom IC1 in order to control the fermenting function of a kimchi fermentor according to the signal from kimchi curing sensor 100 (step 101). After initialization, at step 102 it is determined whether the re-selection of the system function is indicated, and if re-selection is completed, the corresponding function is stored in the memory ( step 103 ). On the contrary, if re-selection is not executed, step 102 is moved into step 104 to judge whether the fermenting function is selected. If the fermenting function is not selected, the temperature in the refrigerating chamber is adjusted at the predetermined temperature (step 105). Then if the fermenting function is selected, step 104 is moved into step 106 to judge whether the fermenting function is appointed to operate at the strong mode.

If the kimchi fermenting selection is the strong mode, micom IC1 outputs the low level signal from its terminal 04 (step 107). Thereafter at step 108 there is judged whether the signal from kimchi curing sensor 100 is considered the third peak point. If the signal is not signal produced at the third peak point, step 108 is moved into step 114 to continue fermentation. But in case of reaching the third peak point, at step 109 micom IC1 counts the predetermined delay time to identify the status of the third peak point, and at step 109 judges whether the delay period has elapsed. If the delay period has expired, step 109 is transferred into step 10 to cancel the fermenting function, and if the delay time is not ended, at step 119 the temperature in the refrigerating chamber is adjusted at the predetermined fermenting temperature.

On the other hand, if the kimchi fermenting operation is not in the strong mode, step 106 is moved into step 111 to judge whether the kimchi fermenting operation is in the weak mode. If fermenting is weak, micom IC1 outputs the low level signal from its terminal O6 and continues to allow kimchi to be fermented (step 112).

While the kimchi fermentor is operated to ferment kimchi, micom IC1 judges at step 114 whether the predetermined fermenting period, for example one hour or two hours, has elapsed. At this step, if the predetermined period have not ended, the number of air bubbles from kimchi curing sensor 100 is counted at step 115. But if the predetermined period has expired, the number of air bubbles counted so far is divided by two at step 116. Next step 116 is transferred into step 117 to judge whether the divided number of air bubbles is larger than that produced before the predetermined time. If the divided number is larger than the predetermined number (step 118), the divided number is stored. Otherwise step 117 goes on to step 120 to judge whether this judgement with respect to the number of air bubbles is originally accomplished. Therefore, if the judgement of the number of the air bubbles is firstly executed, this judgement time point is considered as the first peak point with respect to the production of the air bubbles (step 121). But if the judgement of air bubbles is not the first, step 121 goes into step 122 to judge whether the number of air bubbles is secondly produced at the peak point. If the number of air bubbles is reaching the second peak point, at step 123 this peak point is stored as the main peak status. Step 123 is moved into step 124 to judge whether the fermenting selection is appointed as the weak mode. If kimchi fermenting mode is not set at the weak mode, step 123 is moved into step 119. On the contrary, if kimchi fermenting mode is set at the weak mode, step 124 goes on step 127 to cancel kimchi fermenting function, and again is moved into step 104 to adjust the temperature in the refrigerating chamber at the predetermined temperature.

But if the number of air bubbles is not judged as the second peak point at step 122, step 122 goes on into step 125 to store the peak point as the third peak point. Next step 125 goes into step 126 to judge whether the fermenting appointment is the standardization mode. If the kimchi fermenting status is not standard, step 126 is transferred into step 119 and otherwise transferred into 127 which cancels kimchi fermenting function.

Therefore, when the kimchi fermentor is turned on by applying the power source, micom IC1 judges the temperature in the refrigerating chamber by the signal receive from temperature sensor TH to maintain the temperature of the rerfigerating chamber at the predetermined temperature, for example 25° C., suitable for kimchi fermentation according to the prior art method. If the temperature of the refrigerating chamber is higher than the predetermined temperature, the output O1 of micom IC1 becomes high enough to turn transistor Q4 on, so that compressor COMP is operated. But, if the temperature of the refrigerating chamber is lower than the predetermined temperature, the output O2 of micom IC1 becomes high enough to turn transistor Q2 on, so that heater H is operated, while output O3 also is becoming high enough to operate the motor of fan F, so that the temperature of the refrigerating chamber is uniformly distributed to prevent parts of the kimchi from curing severely or the occurrence of undesirable tastes. That is, if the function of the kimchi fermentor is set for kimchi fermenting, the constant temperature suitable for kimchi fermenting, for example 25° C., is maintained. If the storage function is selected, the constant temperature suitable for storing kimchi, for example 5° C., is maintained.

Also, a kimchi curing degree may be selected among the degrees of the strong, the standard and the weak to meet the user's taste using fermenting key K1. From the first time, if the user wants to use only the refrigerating function with the fermenting function being cancelled, he can cancel the fermenting function using fermenting cancelling key K2. The function selection of kimchi fermentor is represented by light emitting diode L1–L4, each of which is lit, respectively, when the outputs 01–07 of micom IC1 are becoming low to sink the current.

Accordingly, the present invention may be constructed as a home kimchi fermentor as well as an industrial kimchi fermentor. Also this kimchi fermentor can be used in places suitables for mass feeding such as the restaurants, hospitals, boarding houses and barracks, where mass production of kimchi is required. Also it is known that by using the present invention various natural food fermenting foodstuffs may also be automatically prepared.

What is claimed is:

1. A kimchi fermentor, comprising:
   a kimchi case provided with a kimchi curing sensor for producing an electrical signal representing values of kimchi curing variables during curing;
   means for affecting temperature ambient to the kimchi case;
   heating means for inducing kimchi within said case to proceed toward fermentation;
   a temperature sensor producing an electrical signal indicative of the temperature ambient to the kimchi case;
   cooling means for maintaining said kimchi case in a storing mode after completion of kimchi curing;
   a fermenting barrel provided with said temperature affecting means, said temperature sensor, said curing sensor, said heating means and cooling means;
   a fermenting control system for generating control signals on a basis of input signals received from said temperature sensor and said kimchi curing sensor installed in said fermenting barrel; and
   a relay operating portion for controlling operation of said heating means and said cooling means according to the control signals.

2. The kimchi fermentor of claim 1, wherein said curing sensor comprises:
   air bubble collecting means being in a form of a funnel, for accommodating air bubbles from said kimchi case;
   air bubble homogenium means including a tube having one end connected to received air bubbles from said collecting means; and
   measuring means for measuring the number of said air bubbles, said measuring means including a photo-interrupter operated by air bubbles accommodated by said air bubble homogenium means and a binary counter for counting the triggering frequency of said photo-interrupter when said photo-interrupter is operated.

3. The kimchi fermentor as set forth in claim 1, wherein said photo-interrupter includes an opto-coupler, and a reflecting film installed in said measuring means and mounted opposite to said photo-interrupter.

4. A food processing device as set forth in claim 2, wherein said binary counter comprises a microprocessor.

5. A kimchi fermentor as claimed in claim 1, wherein said temperature affecting means comprises a fan and said cooling means comprises a compressor, the fan and the compressor forming a refrigerator.

6. The fermentor of claim 1, wherein said curing sensor comprises means for monitoring gaseous phase emissions from said case.

7. The fermentor of claim 1, wherein said curing sensor comprises means for counting bubbles emanating from said case.

8. The fermentor of claim 6, wherein said monitoring means comprises means for counting bubbles emanating from said case.

9. The fermentor of claim 1, wherein said curing sensor comprises means for converting said gaseous phase emissions into a uniform size of bubbles.

10. The fermentor of claim 1, wherein said curing sensor comprises means for converting said gaseous phase emissions into a uniform size of bubbles.

11. The fermentor of claim 7, wherein said curing sensor comprises means for converting said gaseous phase emissions from said case into said bubbles, with said bubbles characterized by uniformity of size.

12. The fermentor of claim 8, wherein said curing sensor comprises means for converting said gaseous phase emissions into said bubbles, with said bubbles characterized by uniformity of size.

13. The fermentor of claim 1, wherein said curing sensor comprises:

means for collecting gaseous phase emission from kimchi within said case;

means connected to receive said gaseous phase emission from said collecting means, for rendering a uniform size of bubbles; and means for counting said bubbles.

14. The fermentor of claim 1, wherein said control system comprises:

first means for converting said electrical signal representing values of kimchi curing variables into a pulse signal; and means receiving said pulse signal and said electrical signal indicative of the temperature, for determining the state of curing of kimchi within the case and controlling said relay operating portion on the basis of said state to switch said fermentor into said storing mode.

15. The fermentor of claim 6, wherein said control system comprises:

first means for converting said electrical signal representing values of kimchi curing variables into a pulse signal; and means receiving said pulse signal and said electrical signal indicative of the temperature, for determining the state of curing of kimchi within the case and controlling said relay operating portion on the basis of said state to switch said fermentor into said storing mode.

16. The fermentor of claim 9, wherein said control system comprises:

first means for converting said electrical signal representing values of kimchi curing variables into a pulse signal; and means receiving said pulse signal and said electrical signal indicative of the temperature, for determining the state of curing of kimchi within the case and controlling said relay operating portion on the basis of said state to switch said fermentor into said storing mode.

17. The fermentator of claim 12, wherein said control system comprises:

first means for converting said electrical signal representing values of kimchi curing variables into a pulse signal; and means receiving said pulse signal and said electrical signal indicative of the temperature, for determining the state of curing of kimchi within the case and controlling said relay operating portion on the basis of said state to switch said fermentor into said storing mode.

* * * * *

UNITED STATES PATENT AND TRADEMARK OFFICE
CERTIFICATE OF CORRECTION

PATENT NO. : 5,142,969
DATED : 1 September 1992
INVENTOR(S) : Jae-Kun CHUN It is certified that error appears in the above-identified patent and that said Letters Patent is hereby corrected as shown below:

Claim 1,   Column 12,   Line 9, change "affecting" to --maintaining--.

Claim 2,   Column 12,   Line 24, change "received" to --receive--.

Signed and Sealed this

Fourteenth Day of September, 1993

Attest:

BRUCE LEHMAN

*Attesting Officer*   *Commissioner of Patents and Trademarks*